(12) United States Patent
Riffe

(10) Patent No.: US 7,181,992 B1
(45) Date of Patent: Feb. 27, 2007

(54) TRIPPING AND RE-COCKING MECHANISM AND APPARATUS

(76) Inventor: Daniel L. Riffe, 3088 Lake Hollywood Dr., Los Angeles, CA (US) 90068

(*) Notice: Subject to any disclaimer, the term of this patent is extended or adjusted under 35 U.S.C. 154(b) by 103 days.

(21) Appl. No.: 10/766,626

(22) Filed: Jan. 27, 2004

(51) Int. Cl.
G05G 1/04 (2006.01)

(52) U.S. Cl. .................. 74/522; 74/526; 74/532

(58) Field of Classification Search .............. 74/519, 74/522, 526, 532; 73/8, 9
See application file for complete search history.

(56) References Cited

U.S. PATENT DOCUMENTS

| | | | |
|---|---|---|---|
| 5,358,266 A * | 10/1994 | Roth et al. ............... | 280/304.1 |
| 5,904,218 A * | 5/1999 | Watkins ..................... | 180/209 |
| 6,427,891 B1 * | 8/2002 | Anderson et al. ......... | 224/536 |
| 6,681,614 B1 * | 1/2004 | Riffe ........................... | 73/9 |

* cited by examiner

Primary Examiner—David M. Fenstermacher

(57) ABSTRACT

A tripping and re-cocking mechanism (202) is applied to an apparatus (200) by which a shifted apparatus (200) is re-positioned for operation after having shifted from its operational mode. A pivot mount (205) of a second-class lever (204) is connected to a member or casting (209) of apparatus (200). At the point of resistance of lever (204) a roller bearing (215) cooperates with, by latching onto a platform (217), the platform (217) on a standard (221) that is part of apparatus (200), to cock mechanism (202) so that apparatus (200) is returned to its operational position. The shaft (228) of an energized solenoid (227) releases roller bearing (215) from its latched seat on platform (217) in the operation of apparatus (200) thereby shifting it to a non-operational position. Arm (232) re-cocks mechanism (202) to shift apparatus (200) again into its operational position.

13 Claims, 5 Drawing Sheets

US 7,181,992 B1

TRIPPING AND RE-COCKING MECHANISM AND APPARATUS

TECHNICAL FIELD

This invention relates to a tripping and re-cocking mechanism that is adaptable to a frame of a structure of an apparatus by which the apparatus is repositioned for its next cycle or step of operation.

BACKGROUND TO THE INVENTION

In the disclosure pertaining to U.S. Pat. No. 6,681,614, granted Jan. 27, 2004, Apparatus for Testing Co-Efficient of Friction of A Road Surface, the frame of the apparatus is re-positioned by hand for its next cycle or operation. This invention is an improvement over the tripping and the manual re-cocking of the mechanism in the noted patent as well as providing for a mechanism that is suitable for efficiently re-positioning a variety of apparata which require re-positioning after a cycle or step of operation.

In the disclosure of the noted patent, a tripping mechanism mounted on the rear of the apparatus releases the apparatus in its cycle or operation from an upper position to a lower position. The apparatus is then repositioned to its upper or operational position by hand-raising the rear end of the apparatus so that its tripping mechanism would once again be cocked for the next cycle or step of operation of the apparatus.

SUMMARY OF THE INVENTION

This invention is an advance over the technique disclosed in the noted patent that trips the release of a frame and its apparatus and re-sets or re-positions by hand the frame and its apparatus (this invention not to be understood as being limited to the apparatus disclosed in the noted patent). This invention is found in a tripping and re-cocking mechanism for an apparatus by actuation of a pivotal arm about a standard which with a pivotal link is connected to the frame of the apparatus, such actuation causing a re-cocking of the tripped mechanism thus re-positioning the released frame and its apparatus into its operational mode. The re-cocking results in the apparatus being placed into its re-set position for another cycle or step of operation. A bearing, preferably a roller bearing, is mounted on the free end of a second-class lever and is seated in the re-set position on a platform or ledge that is mounted on a standard connected to the apparatus. Means, connected to the frame of the apparatus, is provided, for example, a solenoid, for releasing the bearing from its platform or ledge during operation of the apparatus, shifting the apparatus into a non-re-set or different position. With such release, the second-class lever no longer holds the frame and its apparatus in its re-set position; the frame and apparatus shift or drop to a different or lower position. After completion of the cycle or step of operation the frame of the apparatus is re-set by actuation of the pivotal arm. As the arm pivots, the bearing on the free end of the second-class lever reaches the platform or ledge on the standard to re-cock the tripping mechanism and thus re-position the apparatus in preparation for its next cycle or step of operation, and irrespective of the solenoid. The platform or ledge on the standard is lengthwise adjustable so that the frame and apparatus can be raised or lowered to a desired level prior to or after a cycle or step of operation by the apparatus.

An object of this invention is to eliminate a heavy manual technique in shifting the frame and its apparatus to re-set it in its operational mode.

Another object of the invention is to provide a more efficient way to achieve the same result as was attained in its previously generated manner.

A further object of this invention is to combine its subject matter with an apparatus for testing the co-efficient of friction of a road surface.

Yet another object of the invention is to combine its subject matter with apparata different from that of an apparatus for testing the co-efficient of friction of a road surface.

These and other objects and advantages of the invention will become more apparent by a full and complete reading of the following description, its accompanying drawing FIGURES comprising five (5) sheets of five (5) FIGURES, and the appended claims.

BEST MODE FOR CARRYING OUT THE INVENTION

Figure 1:
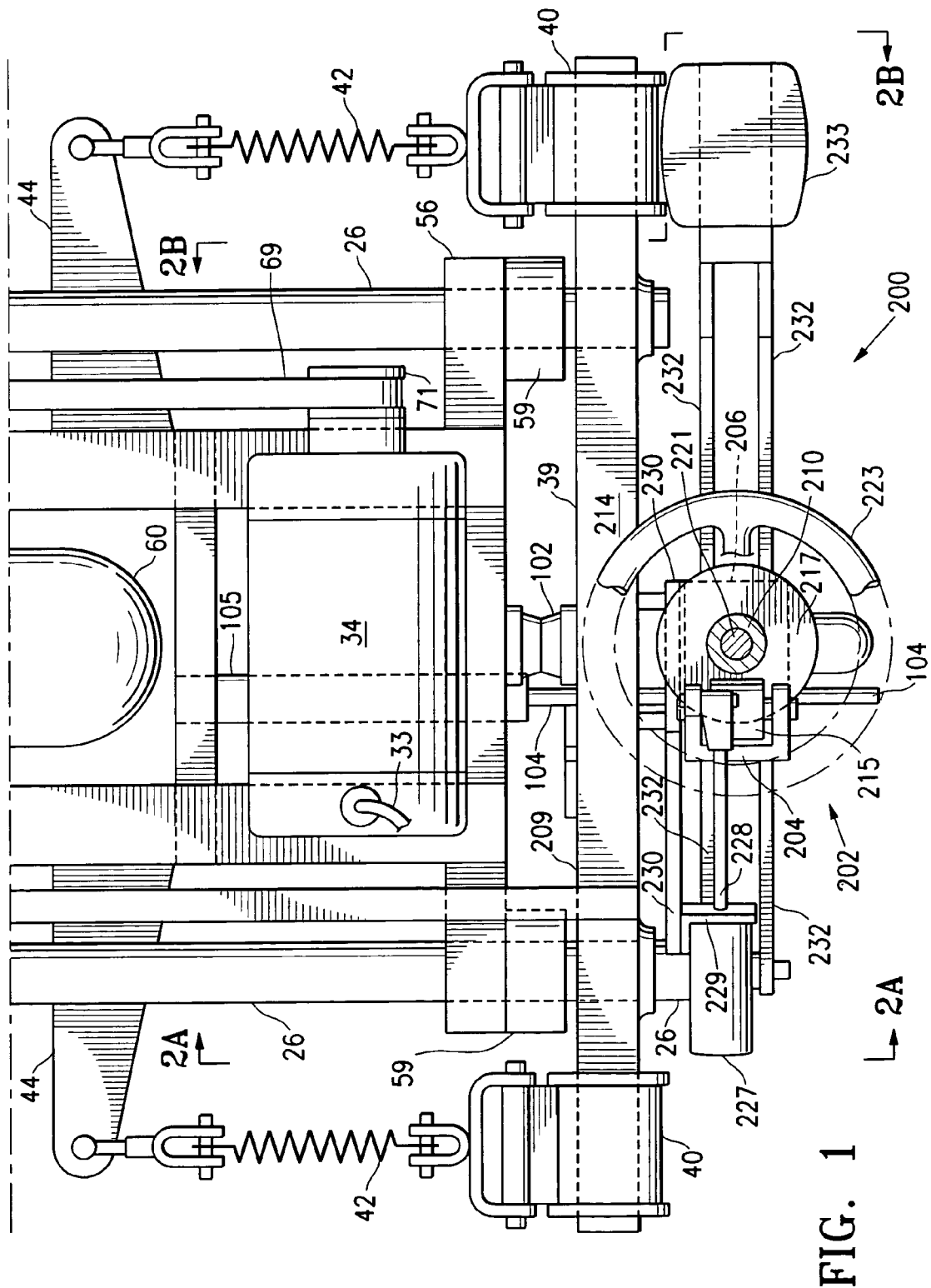
FIG. 1 is a fragmentary plan view of an apparatus and mechanism to which the present invention is applied.
Figure 2A:
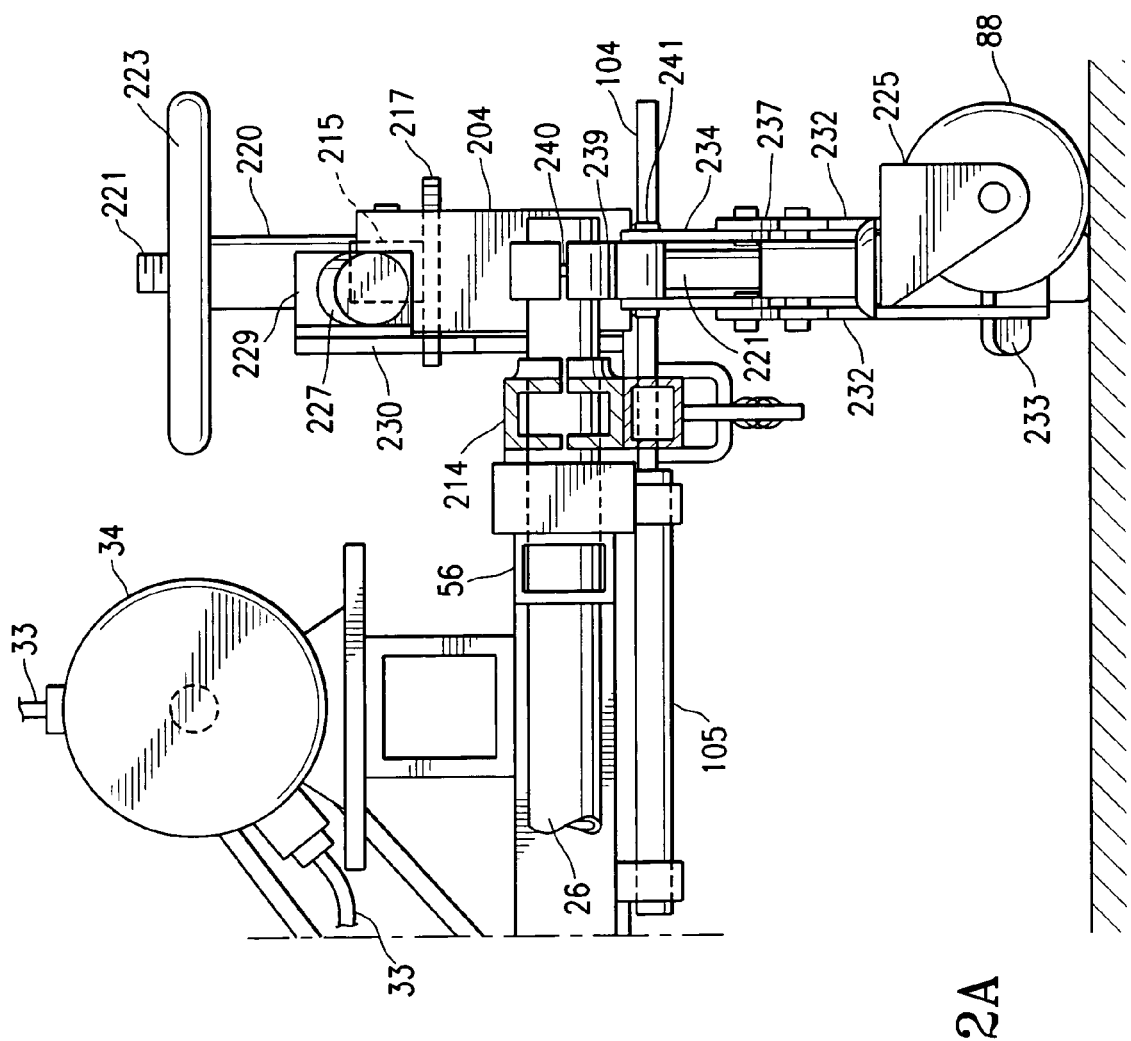
FIG. 2A is a side view of the apparatus and mechanism taken on line 2A—2A of FIG. 1
Figure 2B:
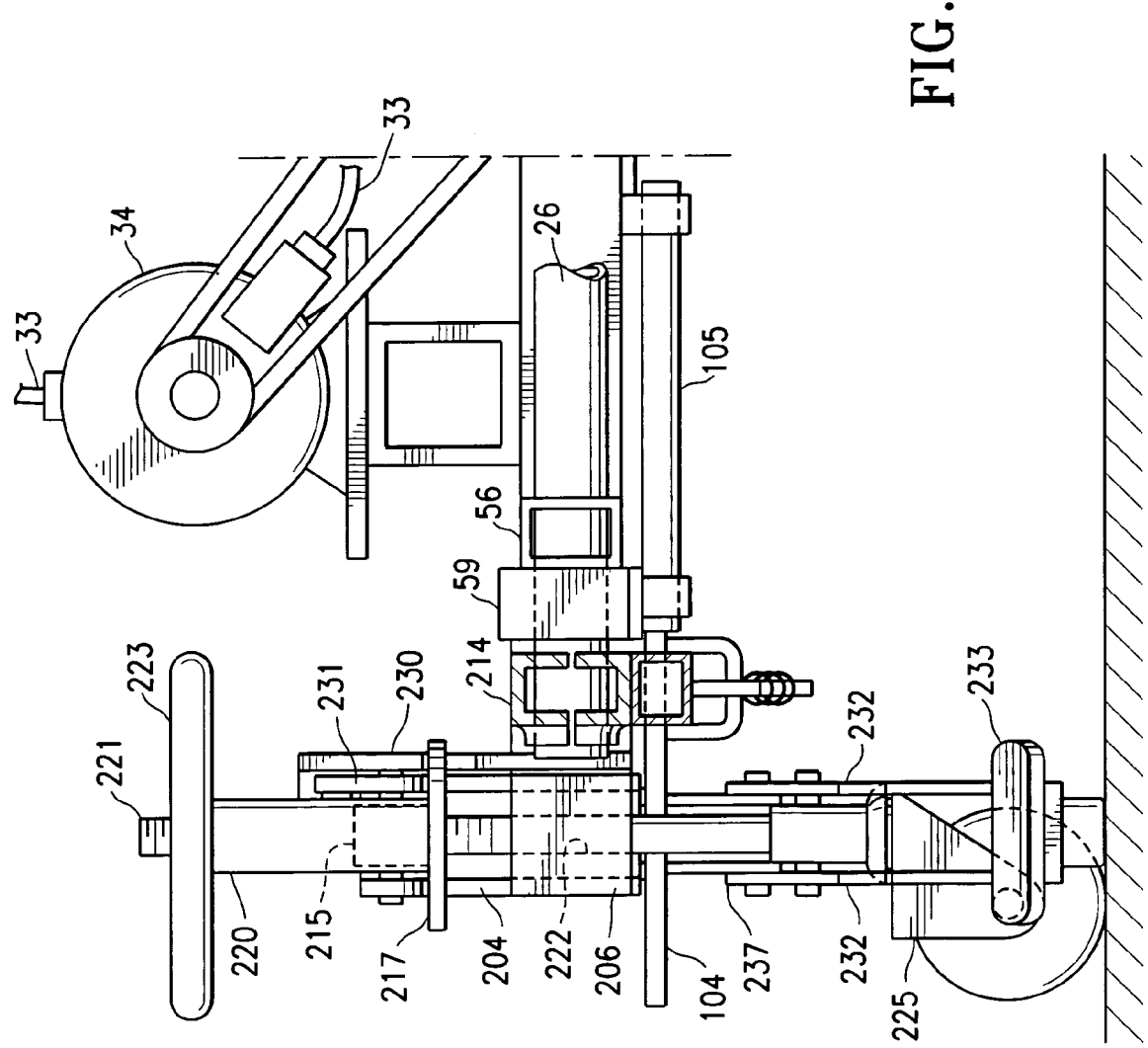
FIG. 2B is a view of the other side of the apparatus and mechanism taken on line 2B—2B of FIG. 1.

Referring now to the drawing FIGURES wherein reference characters correspond to like numerals hereinafter, FIGS. 1–4 illustrate an apparatus 200 to which the tripping and re-cocking mechanism of the present invention is coupled. It should be understood in the reading of this disclosure, reference characters appearing in the drawing less than the numeral 200 refer to reference characters illustrated in the drawing in U.S. Pat. No. 6,681,614 and which correspond to their descriptions of the elements described in that patent. Some are illustrated here to provide clarity in the reading of this disclosure. The apparatus 200 and mechanism 202 of this description is combined with that of the disclosure in U.S. Pat. No. 6,681,614, and to which the subject matter of the present invention is applicable, as well as to other apparata that require a shifting of its frame or structure for operation. It is to be understood that the noted patent's disclosure is incorporated by reference into this disclosure.

Figure 3:
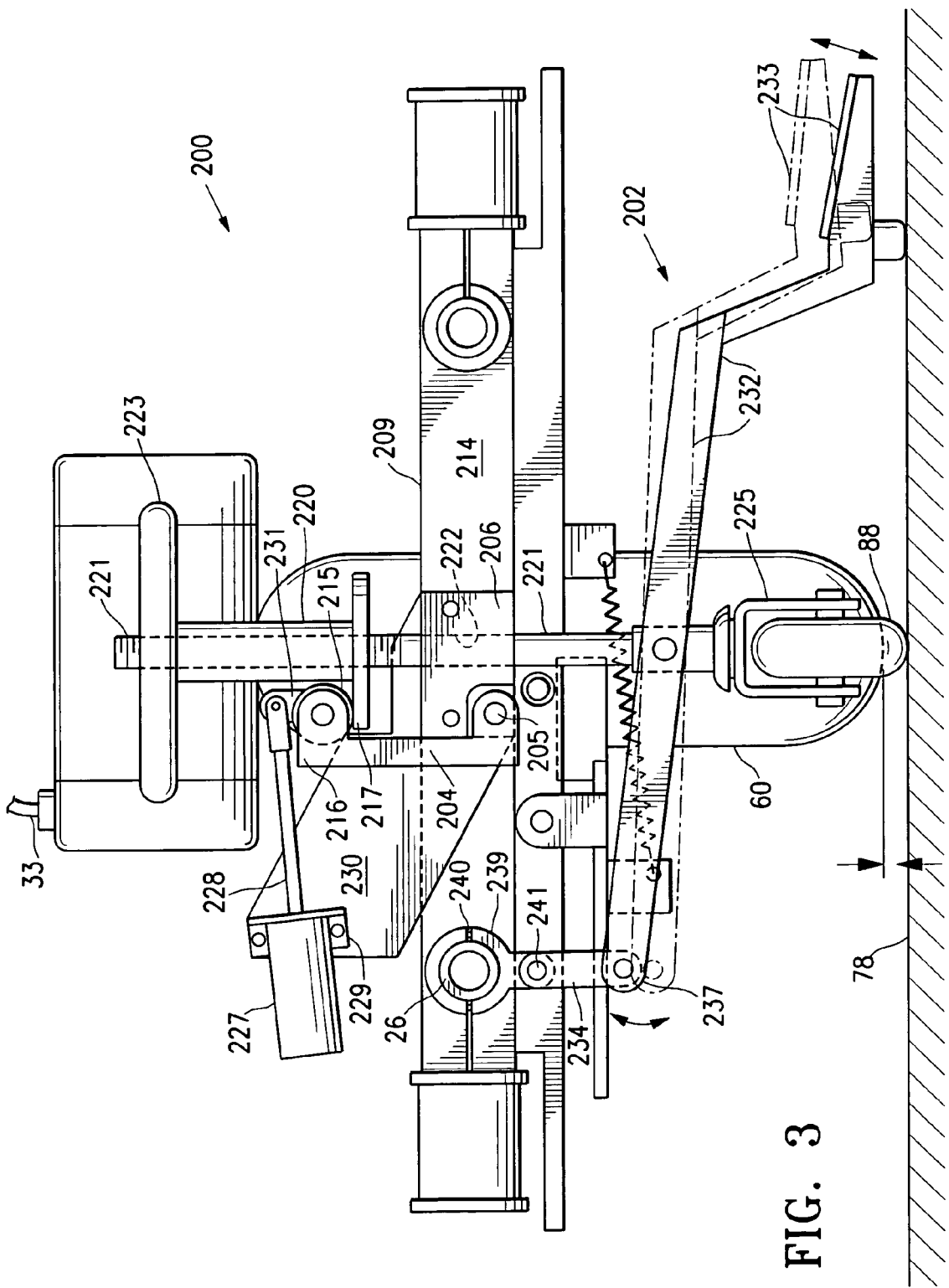
FIG. 3 is an end view of the apparatus of FIGS. 1, 2A, and 2B, illustrating the re-cocked position of the tripping mechanism for the apparatus.
Figure 4:
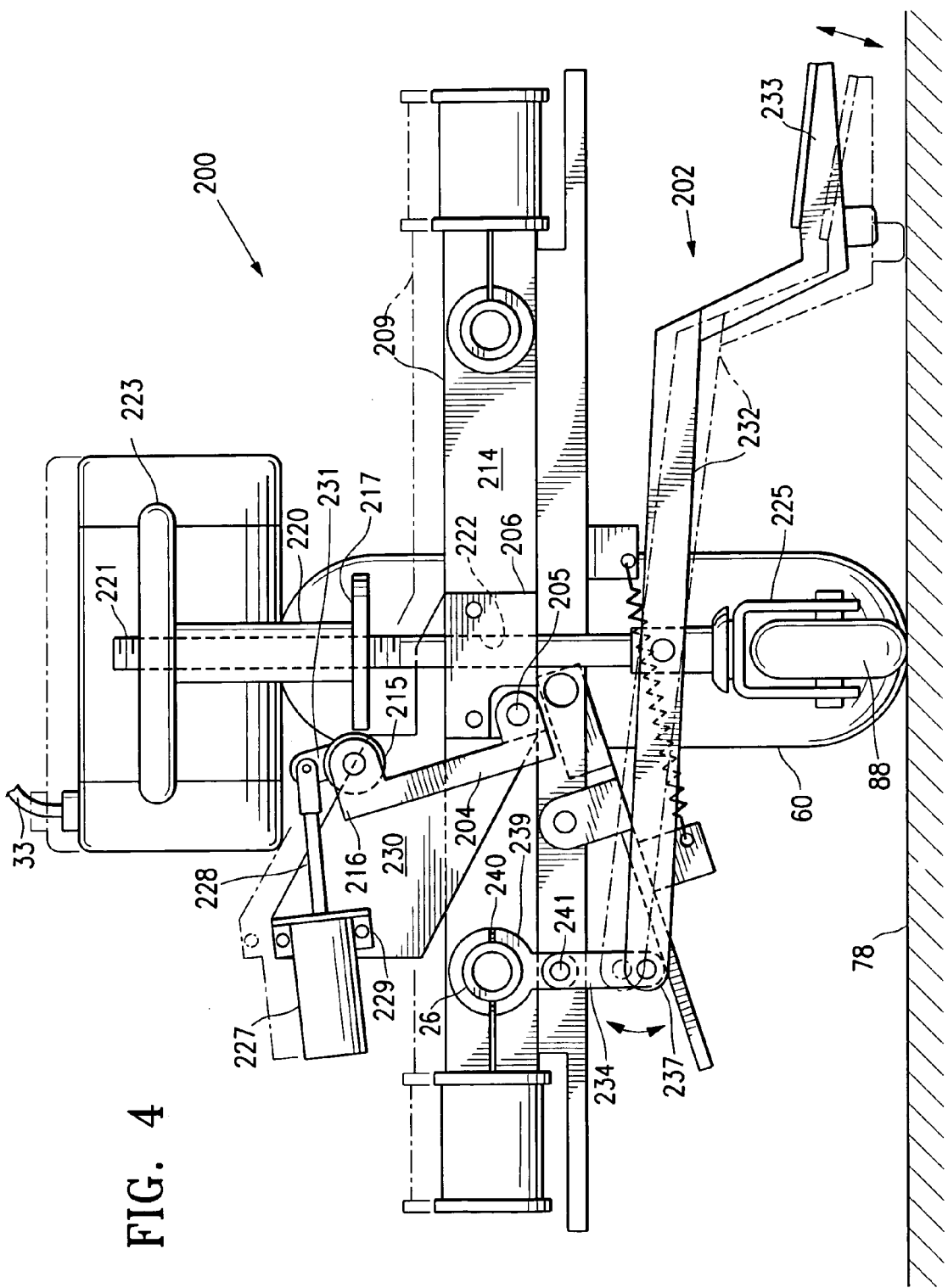
FIG. 4 is an end view of the apparatus of FIGS. 1, 2A and 2B, illustrating the un-cocked position of the tripping mechanism for the apparatus.

Turning to FIGS. 3 and 4, the tripping and re-cocking mechanism 202 of this invention is shown in its cocked mode and in its released mode, respectively. A second-class lever 204 is suitably pivotally mounted as at 205 to a member such as a block 206 secured to or formed as part of a casting 209 that is a member of frame 214 of apparatus 200. A bearing 215, preferably a roller bearing, is suitably secured at the lever's point of resistance 216 opposing its pivotal mount 205. Bearing 215 is seated, FIG. 3, on a platform or ledge 217 that functions in a latching manner on bearing 215. Platform or ledge 217 is formed on or secured to a sleeve 220 threadedly mounted to a threaded standard 221 that projects through a co-operating bore 222 in block 206, thus, connecting standard 221 to frame 214. A handle 223 is suitably secured to sleeve 220 for adjusting the platform or ledge 217 along the length of standard 221. A caster assembly 225, though not necessary should apparatus 200 not be portable or movable, is secured to the bottom of standard 221. It should be understood that the invention is not limited to its application merely to a rear-end caster assembly as illustrated in the disclosure of the noted patent or merely to a rear end of another apparatus.

A solenoid 227 is securely mounted by a flanged support bar 229 bolted to a backing plate 230 which in turn is securely fixed such as by bolting to casting 209, i.e., to frame 214. The solenoid's shaft 228 is connected to a link 231 that is an upwardly extending extension of lever 204 and fixed to bearing 215, so that upon the pull of shaft 228 in the energization of solenoid 227 bearing 215 is linearly displaced from its latched state on platform or ledge 217.

A first-class lever or arm 232 is pivotally mounted to and adjacent to the bottom end of standard 221 and is actuated at its one end at which a foot pedal 233 is mounted for ease in operation of the invention, removing to a considerable extent labor-activated efforts to re-set the position of an apparatus to which mechanism 202 is combined or connected. The one end of a link 234 is pivotally mounted at the other end 237 of arm 232 and the other end of link 234 is pivotally mounted to a split clamp 239 that is tightened about tubular member 26 (see FIGS. 1 and 2 of the noted patent) representing the frame 214 of the drawing herein and to which the subject matter of this invention is applied. Socket-head cap screws 240 connect together the halves of clamp 239 for tightening about tubular member 26. It may be noted that since link 234 pivots in its action about its fulcrum 241 of link 234 associated with split clamp 239, the motion of the fulcrum in the end 237 of arm 232 is an arc and as such arm 232 does have a horizontal component of movement, although in the range of motion of apparatus 200, this horizontal component of movement can be treated as negligible.

In operation of the invention, after apparatus 200 has completed its cycle or operation, its frame, represented by casting 209, is in its lowered or non-operational position. FIG. 4 illustrates the non-operational position of apparatus 200, the bearing 215 of second-class lever 204 unlatched from platform or ledge 217. Further, it maybe noted that tire 60 engages the road surface or floor 78, which reflects that the cycle or step of operation of an apparatus, such as 200, is ended and in which the frame of the apparatus has shifted to its non-operational mode or position. To raise casting 209 and its frame and apparatus 200 to its upper or re-set position, prior to initiation of the next cycle or step of operation for apparatus 200, arm 232 is actuated by depressing foot pedal 233 on pivotal arm 232. Arm 232 pivots about standard 221, FIG. 3, thereby moving its pivotal link 234, and along with it shifts split clamp 239 and its attached casting 209 that is part of the frame 214 of apparatus 200. Concurrently, bearing 215 again seats upon its platform or ledge 217, FIG. 3, re-cocking mechanism 202 and placing apparatus 200 into its operational or re-set mode. It may be noted in FIG. 3 that tire 60 now is elevated above road surface or floor 78, illustrating that apparatus 200 is in its re-set or operational mode. Also, FIG. 4 illustrates that after un-cocking of second-class lever 204, foot pedal 233 on pivotal arm 232 is in its elevated orientation so that mechanism 202 is ready for operation by depressing pedal 233 to once again re-cock second-class lever 204 by which apparatus 200 becomes operational.

Further, in the operation of apparatus 200, solenoid 227, in its energization, pulls its shaft 228 its shaft and in so doing, draws or uncocks bearing 215 from its platform on ledge 217 that is coupled or mounted to standard 221 that is part of apparatus 200. Consequently, frame 214 drops, or shifts, thereby shifting apparatus 200 from its operational to its non-operational position. Elements other than solenoid 228 which perform the same function are contemplated within the scope of this invention.

Apparatus 200 can be elevated to any desired level from road surface or floor 78 by adjusting through the turning of handle 223 about sleeve 220, and thus platform or ledge 217, to any point along the length of threaded standard 221. The depth of an apparatus may require such an adjustment.

Various changes and modifications may be made to mechanism 202 and apparatus 200 without departing or varying from the scope and spirit of the following appended claims of the invention.

INDUSTRIAL APPLICABILITY

The invention is applicable to devices or apparata in various classes of art and is not limited to devices classified only in Class 73 in the U.S. Patent Office classification of the arts.

I claim:

1. A mechanism for re-cocking from its non-operational position a shifted frame of an apparatus in which the apparatus becomes operational comprising
   standard means connected to the frame,
   latching means mounted on said standard means,
   a second-class lever having a point of resistance and being pivotally-connected to said frame,
   a bearing member mounted at the point of resistance of said second-class lever,
   said bearing member adapted for seating on said latching means to re-cock the shifted frame from its non-operational to its operational position in the pivotal motion of its second-class lever, and
   pivotal means connected to said standard means for seating said bearing member on said latch means,
   whereby actuation of said pivotal means raises the frame to thereby seat said bearing member on said latching means thereby re-cocking the apparatus into its operational position.

2. The mechanism of claim 1 wherein
   said pivotal means comprises
   arm means pivotally mounted on said standard means and having a first free end and a pivotal link connecting said arm means at its first free end to the frame.

3. The mechanism of claim 2 wherein
   said arm means includes a second free end for its actuation.

4. The mechanism of claim 1 wherein
   said latching means comprises
   a platform and a bearing.

5. The mechanism of claim 4 wherein
   said bearing is a roller bearing.

6. The mechanism of claim 5 wherein
   said latching means is adjustable on said standard means.

7. The mechanism of claim 4 wherein
   said latching means is adjustable on said standard means.

8. The mechanism of claim 4 including
   means for adjusting said latching means on said standard means.

9. The mechanism of claim 8 wherein
   said adjusting means comprises a threaded sleeve fixed to said standard, said standard means being threaded.

10. The mechanism of claim 1 in combination with an apparatus shiftable as a result of its operation in a cycle or step of such operation, said apparatus including a frame having a member, said mechanism operatively connected to said member.

11. A re-cocking mechanism to re-set into its operational mode a shifted apparatus having a frame and standard means, comprising a pivotal arm operatively connected through said standard means to the apparatus, and having at a first end a link adapted to link to a member on the frame, a second-class lever pivotally mountable and operatively connectable to the frame, latching means in the form of a platform mountable on said standard means, a bearing on said second-class lever at its point of resistance for seating on said platform thereby cocking said mechanism by which the apparatus is re-set, said pivotal arm actuable at a second end for causing said bearing to latch onto said platform thereby re-setting the apparatus.

12. The re-cocking mechanism of claim 11 in combination with a shiftable apparatus, said apparatus including means for releasing said bearing from its latched seat on said platform in operation of said apparatus whereby said apparatus shifts to a non-operational position upon actuation of said releasing means.

13. The combination of claim 12 wherein said releasing means comprises a solenoid operatively connected to said second-class lever.

* * * * *